United States Patent [19]
Link et al.

[11] Patent Number: 6,120,528
[45] Date of Patent: Sep. 19, 2000

[54] NIPPLE ASSEMBLY WITH ENDOSCOPE

[75] Inventors: Dana Thompson Link, Cincinnati, Ohio; Anthony M. Sacchetti, Weymouth; Lewis H. Marten, Westwood, both of Mass.; Nicholas Tscalas, Coral Springs, Fla.

[73] Assignees: Hood Laboratories, Pembroke, Mass.; Children's Hospital Research Foundation, Cincinnati, Ohio

[21] Appl. No.: 09/185,216

[22] Filed: Nov. 3, 1998

[51] Int. Cl.⁷ ........................................ A61J 17/00
[52] U.S. Cl. .................... 606/236; 606/234; 600/114; 128/847
[58] Field of Search .................... 600/114, 115, 600/121, 127; 128/847, 848; 606/234, 235, 236

[56] References Cited

U.S. PATENT DOCUMENTS

| | | |
|---|---|---|
| 2,243,529 | 5/1941 | Grossman et al. . |
| 2,824,561 | 2/1958 | Mueller . |
| 3,051,176 | 8/1962 | Alberti . |
| 3,893,446 | 7/1975 | Miller . |
| 4,495,945 | 1/1985 | Liegner ................. 128/200.26 |
| 4,850,953 | 7/1989 | Haber et al. . |
| 5,007,900 | 4/1991 | Picha et al. . |
| 5,366,478 | 11/1994 | Brinkerhoff et al. . |
| 5,375,593 | 12/1994 | Press . |
| 5,503,625 | 4/1996 | Plass . |
| 5,545,179 | 8/1996 | Williamson, IV . |
| 5,645,565 | 7/1997 | Rudd et al. . |
| 5,649,540 | 7/1997 | Alvarez et al. ........................... 128/848 |
| 5,665,064 | 9/1997 | Bodicky et al. . |
| 5,830,235 | 11/1998 | Standley ................................... 606/234 |
| 5,981,165 | 4/1999 | Buckner ................................... 606/234 |

*Primary Examiner*—Linda C. M. Dvorak
*Assistant Examiner*—Brad C. Blaise
*Attorney, Agent, or Firm*—Pitney, Hardin, Kipp & Szuch, LLP

[57] ABSTRACT

A device for allowing visual examination of the swallowing of fluids by an infant which includes a nipple mounted housing, a feeding tube for feeding fluid into the nipple, openings in the nipple to allow the fluid to pass or be sucked therethrough, a further opening centrally located in the nipple through which an endoscope is passed to allow for such visual examination.

12 Claims, 1 Drawing Sheet

NIPPLE ASSEMBLY WITH ENDOSCOPE

FIELD OF THE INVENTION

The present invention involves a device for diagnostic purposes, particularly with regard to infants or small children which allows for the visual observation of swallowing of fluids.

BACKGROUND OF THE INVENTION

Adults swallow without thinking. It is, however, a complex process whereby food or liquid is transferred from the mouth through the pharynx and esophagus into the stomach. The first stage of swallowing is voluntary during which the food or fluid passes from the mouth into the oropharynx principally by the movement of the tongue. The second stage of swallowing is involuntary and involves the contraction of the walls of the pharynx. Breathing stops and contraction of three constrictor muscles move the food or liquid through the oral and laryngeal part of the pharynx. The soft palate is elevated to prevent food from entering the nasopharynx.

Swallowing dysfunction or dysphagia, when it occurs in adults, can be observed by a physician using a scope requesting the patient to swallow. Alternatively, a patient can swallow a solution containing barium whilst being x-rayed.

However, for infants or very small children, barium and x-rays are not practical nor desirable. In the situation of new borns particularly, it is often important to observe the suck-swallow reflex to observe its synchronization to confirm the existence or non-existence of aspiration.

Accordingly, there exists a need for a device for allowing a physician to observe the swallowing of fluids in new borns and infants to insure that aspiration is not occurring.

SUMMARY OF THE INVENTION

It is therefor a principal object of the invention to provide a device which allows for the observation of swallowing in new borns or infants.

It is a further object to provide for such a device which is relatively simple yet practical when dealing with a new born or infant.

It is a yet further object to provide for such a device that avoids the use of x-rays or barium type solutions.

These and other objects will be realized by the present invention's use of a nipple assembly having an endoscope passing therethrough to allow the observation of swallowing in an infant. In this regard, the nipple includes openings which allow for fluid to pass therethrough during sucking thereon. This allows for a controlled introduction of fluid, preferably colored (as compared to clear), to allow for such observation. The nipple holders include a guide means to allow for the positioning of the endoscope along with a control valve to regulate introduction of the fluid.

BRIEF DESCRIPTION OF THE DRAWINGS

Thus by the present invention its objects and advantages will be realized, the description of which should be taken in conjunction with the drawings wherein.

DETAILED DESCRIPTION OF THE PREFERRED EMBODIMENT

Figure 2:
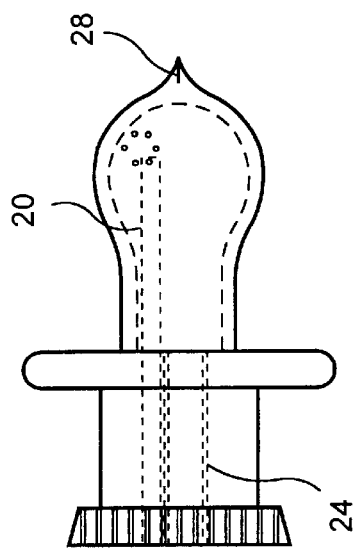
FIG. 2 is a side sectional view of the nipple assembly without the endoscope or feeding valve incorporating the teachings of the present invention.
Figure 5B:
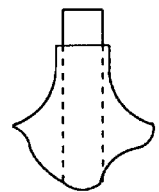
FIG. 5B is a side sectional view of the endoscope inserted through the nipple opening.
Figure 5A:
FIG. 5A is a side perspective view of the nipple opening.
Figure 1:
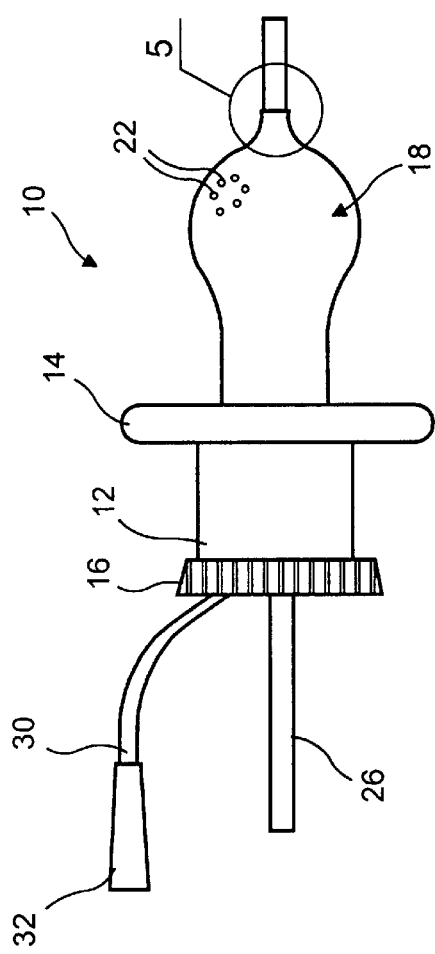
FIG. 1 is a side perspective view of the nipple assembly showing the endoscope and feeding valve incorporating the teachings of the present invention.
Figure 4:
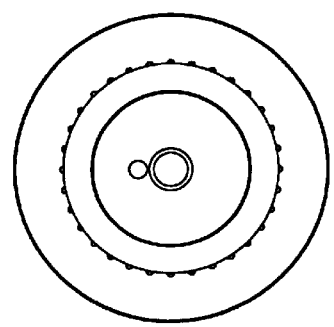
FIG. 4 is a rear perspective view of the nipple assembly shown in FIG. 2 incorporating the teachings of the present invention.
Figure 3:
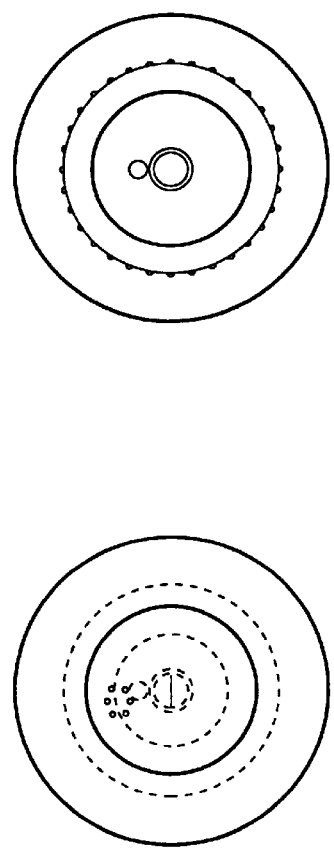
FIG. 3 is an enlarged front, partially sectional, view of the nipple assembly shown in FIG. 2 incorporating the teachings of the present invention.

Turning now more particularly to the drawings, there is shown the nipple assembly 10. The assembly 10 includes a cylindrical housing 12 having an enlarged circular flange or shield 14, both of which may be made out of a plastic or silicone material. Rearward of flange 14 is a rigid textured gripping surface 16. At the forward end of the assembly 10 is a bulb or nipple 18 which may be made of silicone 50 durometer or other material suitable for purpose.

The assembly 10 includes a feeding tube 20 which passes therethrough and discharges adjacent a plurality of off-centered micro holes or openings 22 in the bulb 18. Tube 20 may be rigidly affixed to the assembly 10. The fluid passing through tube 20 is intended to only pass through and out of openings 22.

Also included in assembly 10 is an endoscope guide 24 in which an endoscope 26 is intended to be positioned in a friction fit engagement. The endoscope 26, which may be 5 mm or other size suitable for purpose, is inserted through the guide 24 and interior of bulb 18 out through a single forward slit or opening 28 which is of a volcano style or other type opening providing an air seal therebetween.

Coupled to the feeding tube 20 is a further tube arrangement 30 which is coupled to a source of baby formula or fluid (not shown) which is preferably colored and includes a valve 32 to regulate the flow of fluid. This may be a standard Luer lock valve or may be any other type valve suitable for purpose.

As can be seen, when the nipple or bulb 18 is sucked on by the infant, it receives the colored formula which is fed out of opening 22 in a controlled fashion. The endoscope 26 can be inserted and the position of the end of it can be adjusted by sliding it in the guide 24 whilst grasping the assembly 10 at surface 16. The flange 14 also assists in this regard. Accordingly, the infant's sucking and swallowing reflex can be readily observed by way of the endoscope while the infant is feeding and the occurance of aspiration or non-aspiration determined.

Thus by the present invention its objects and advantages are realized and, although a preferred embodiment has been disclosed and described in detail herein, its scope should not be limited thereby rather its scope should be determined by that of the appended claims.

What is claimed is:

1. A device for visually observing the swallowing of fluids by an infant comprising:
    a nipple for sucking on by an infant;
    a means for feeding a fluid into said nipple;
    a first opening for allowing fluid to pass out of the nipple; and
    a second opening in the nipple through which an endoscope type device passes so as to allow the visual observation of the swallowing of the fluid by the infant.

2. The device as described in claim 1 wherein said nipple is hollow and further including a housing on which the nipple is mounted.

3. The device as described in claim 2 wherein the nipple is made from silicone and the housing is made from plastic.

4. A device for visually observing the swallowing of fluids by an infant comprising:
- a nipple for sucking on by an infant;
- a means for feeding a fluid into said nipple;
- a first opening for allowing fluid to pass out of the nipple;
- a second opening in the nipple through which an endoscope type device passes so as to allow the visual observation of the swallowing of the fluid by the infant; and
- a housing on which the nipple is mounted, said housing including a guide opening to support an endoscope and allows it to pass into the nipple and out the distal end thereof.

5. The device as described in claim 4 which includes a feeding tube mounted on the housing and positioned within the nipple so as to allow the flow of fluid to the first opening.

6. The device as described in claim 5 wherein said second opening is positioned in the center of the nipple and the first opening is offset with respect thereto.

7. The device as described in claim 6 wherein said first opening includes a plurality of openings.

8. The device as described in claim 6 wherein said housing includes an enlarged flange rearward of the nipple and a gripping surface rearward of the flange.

9. The device as described in claim 5 which further includes a means for controlling the flow of fluid in the feeding tube.

10. The device as described in claim 4 wherein said housing includes an enlarged flange rearward of the nipple and a gripping surface rearward of the flange.

11. The device as described in claim 10 which further includes a means for controlling the flow of fluid in the feeding tube.

12. The device as described in claim 4 wherein the nipple is made from silicone and the housing is made from plastic.

* * * * *

UNITED STATES PATENT AND TRADEMARK OFFICE
CERTIFICATE OF CORRECTION

PATENT NO. : 6,120,528
DATED : September 19, 2000
INVENTOR(S) : Dana Thompson Link, Anthony M. Sacchetti, Lewis H. Marten, Nicholas Tsaclas It is certified that error appears in the above-identified patent and that said Letters Patent are hereby corrected as shown below:

On the cover page, under [75] Inventors, line 5, change "Tscalas" to --Tsaclas--.

Signed and Sealed this

Fifteenth Day of May, 2001

*Attest:*

NICHOLAS P. GODICI

*Attesting Officer*  Acting Director of the United States Patent and Trademark Office